United States Patent
Keane

[19]

[11] Patent Number: 5,854,683
[45] Date of Patent: *Dec. 29, 1998

[54] OPTICAL WEB DEFECT DETECTION SYSTEM

[76] Inventor: Barry P. Keane, 1704 Keowee Lakeshore Dr., Seneca, S.C. 29672

[ * ] Notice: This patent issued on a continued prosecution application filed under 37 CFR 1.53(d), and is subject to the twenty year patent term provisions of 35 U.S.C. 154(a)(2).

[21] Appl. No.: 957,535

[22] Filed: Oct. 24, 1997

[51] Int. Cl.$^6$ ........................................ G01N 21/86
[52] U.S. Cl. ................................ 356/430; 356/238
[58] Field of Search .......................... 356/429, 430, 356/238, 242; 250/559.46

[56] References Cited

U.S. PATENT DOCUMENTS

| | | |
|---|---|---|
| H1616 | 12/1996 | Wolfe . |
| 3,859,538 | 1/1975 | Mannonen ........................ 356/430 |
| 3,958,127 | 5/1976 | Faulhaber et al. . |
| 4,011,457 | 3/1977 | Wolf . |
| 4,131,803 | 12/1978 | Takematsu et al. . |
| 4,414,476 | 11/1983 | Maddox et al. .................. 356/430 |
| 4,656,360 | 4/1987 | Maddox et al. . |
| 4,728,800 | 3/1988 | Surka . |
| 4,788,756 | 12/1988 | Leitner, Sr. . |
| 5,035,030 | 7/1991 | Pellari . |
| 5,243,408 | 9/1993 | Whitman, III . |
| 5,287,742 | 2/1994 | Aihara et al. . |
| 5,497,235 | 3/1996 | Bell . |
| 5,555,611 | 9/1996 | Lyczek . |
| 5,621,220 | 4/1997 | Muehlenbein et al. ................ 356/430 |

OTHER PUBLICATIONS

Manual describing input/output boards, pp. 4, 5 and 32, published before Oct. 24, 1996.

*Primary Examiner*—Richard A. Rosenberger
*Attorney, Agent, or Firm*—Dority & Manning, P.A.

[57] ABSTRACT

An optical web defect detection system includes a light source and a detector disposed with respect to the light source so that the detector receives light modulated by a web moving proximate the light source. The detector outputs a signal corresponding to the modulated light. An adjustment mechanism is in operative communication with the detector to adjust the position of the detector with respect to the web. A control mechanism is in operative communication with the detector and the adjustment mechanism. The control mechanism receives the signal to detect a defect in the web based thereon and adjusts the position of the detector to optimize reception of the modulated light by the detector.

37 Claims, 8 Drawing Sheets

OPTICAL WEB DEFECT DETECTION SYSTEM

BACKGROUND OF THE INVENTION

The present invention relates to a system for detecting defects in a moving web. Webs, for example textile webs, may often include defects, for example yarn width variations, mispicks, double picks, machine stop marks, and pile irregularities, which are not readily detectable by a human operator. These defects sometimes become apparent only during downstream processing steps, for example dying, or after the fabric is shipped to a customer. According, it is desirable to detect such defects at a relatively early production stage.

Automatic web defect detection systems are known which employ photodetectors disposed with respect to a light source and the moving web to detect defects from the interference between the web and light from the light source. Calibration of such systems so that these photodetectors receive an optimal light signal may sometimes be difficult, particularly as the web or ambient conditions change.

SUMMARY OF THE INVENTION

The present invention recognizes and address the foregoing disadvantages, and others, of prior art constructions and methods.

According, it is an object of the present invention to provide an improved optical web detection system.

It is another object of the present invention to provide an optical web detection system which is self-calibrating to optimally detect light modulated by a moving web.

It is a further object of the present invention to provide an optical web detection system which is self-calibrating to eliminate low-frequency ambient light conditions.

Some of these objects are achieved by an optical web defect detection system. The system comprises a light source and a detector disposed with respect to the light source so that the detector receives light modulated by a moving web proximate the light source. The detector outputs a signal corresponding at least in part to the modulated light. An adjustment mechanism is in operative communication with the detector to adjust the position of the detector with respect to the web. A control mechanism is in operative communication with the detector and the adjustment mechanism. The control mechanism receives the signal to detect a defect in the web based on the signal and adjusts the position of the detector to optimize reception of the modulated light by the detector.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
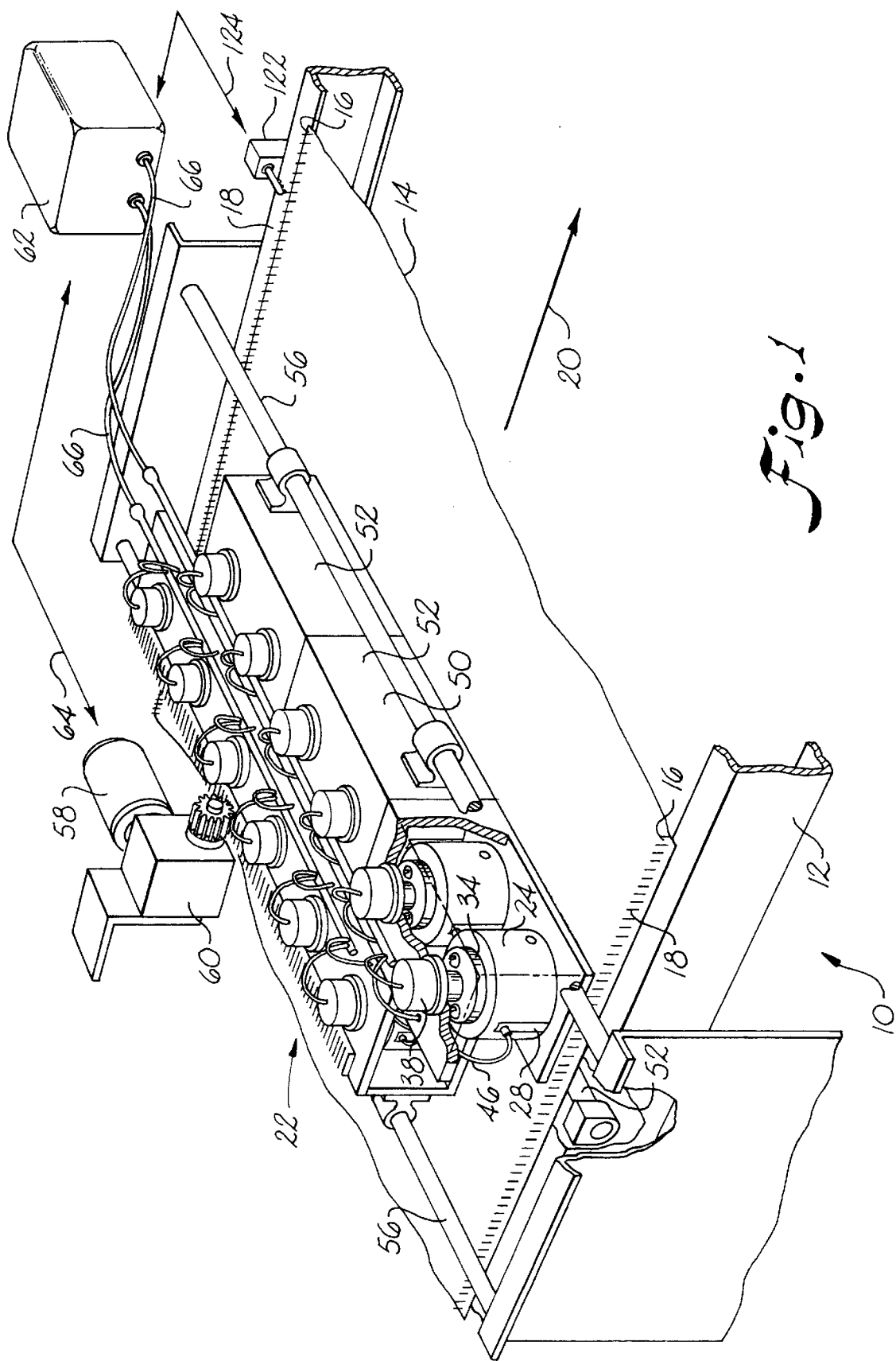
FIG. 1 is a perspective view of an embodiment of an optical web defect detection system constructed in accordance with the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made to the present invention without departing from the scope or spirit of the invention. For instance, features illustrated or described as part of one embodiment can be used on another embodiment to yield a still further embodiment.

The present invention is concerned with an optical web defect detection system. Accordingly, FIG. 1 depicts a web handling system 10 including a frame 12 securing a textile web 14 at selvages 16 by pins 18 to move web 14 in a longitudinal direction indicated at arrow 20. System 10 also includes an optical web defect detection system, indicated generally at 22, which includes a plurality of detectors 24 disposed proximate each other to extend substantially across the web. The detectors extend across the web over that part of the web for which detection of defects is desirable. Thus, for example, the detectors might not extend over the selvages.

Figure 4:
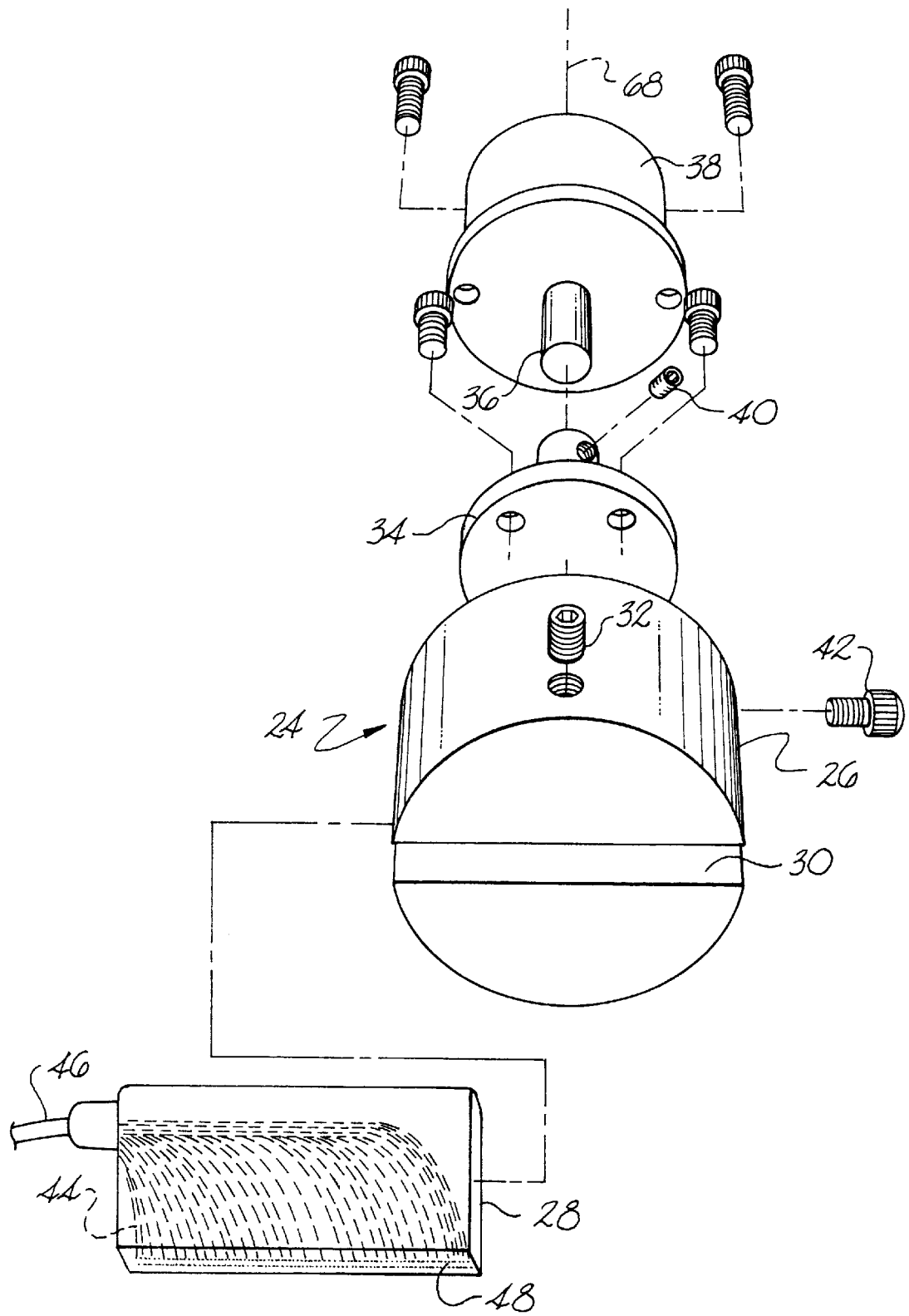
FIG. 4 is an exploded view of an embodiment of a detector device and adjusting motor for use in an optical web defect detection system constructed in accordance with the present invention.

Referring to FIG. 4, a detector 24 includes a housing 26 receiving an elongated optical sensor 28 in a slot 30. Sensor 28, for example a IR2.53S sensor available from Danner Engineering, is secured in slot 30 by a set screw 32. A hose clamp may also be used to secure the sensor. A cap 34 is mounted to the top of housing 26 to receive a shaft 36 of a servo motor 38. Shaft 36 is secured in cap 34 by set screw 40 so that detector 24 rotates with shaft 36. A screw 42 is received in housing 26 so that the screw's end extends outward from the housing to act as a stop to limit rotation of the detector, as is discussed in more detail below.

Sensor 28 includes a plurality of fiber optic elements 44 supplied by a cable 46 and fanning out within the sensor so that the ends of the fiber optic element extend along the longitudinal sensor surface 48 of sensor 28.

Figure 2:
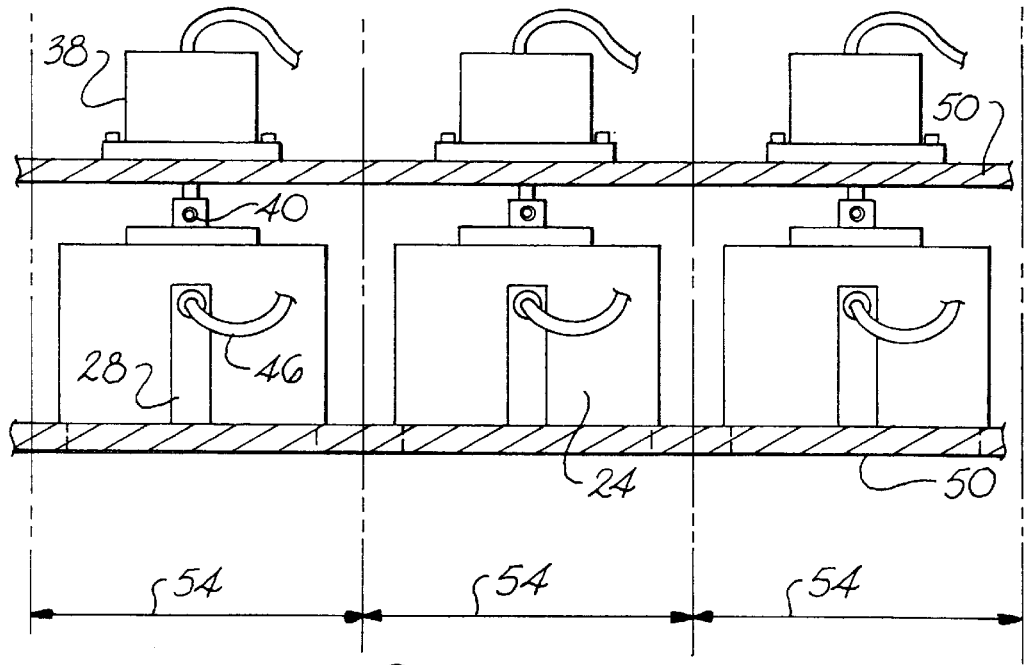
FIG. 2 is a partial plan view of the optical web defect detection system as in FIG. 1.
Figure 3:
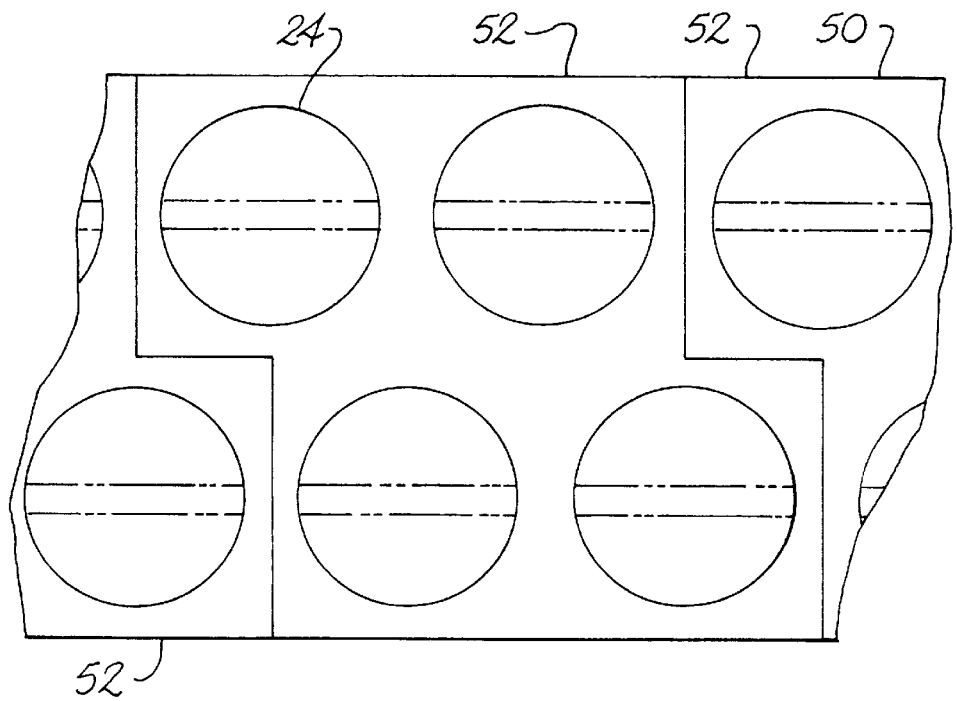
FIG. 3 is a partial bottom view of an embodiment of an optical web defect detection system constructed in accordance with the present invention.

Referring to FIGS. 1, 2 and 3, a plurality of detectors 24 are disposed in two rows in a frame 50 extending across the width of web 14. Frame 50 has a flat bottom to flatten the web passing beneath the detectors. A pair of florescent lights 52 (one of which is shown in FIG. 1) are secured to frame 12 and extend beneath web 14 beneath the respective rows. It should be understood, however, that any suitable light source, for example halogen bulbs beneath each detector, may be used. Referring to the partial bottom view of a frame 50 in FIG. 3, the detectors of one row are staggered with respect to those of the other row so that the sensor surfaces 48 receive light from the respective lights 52, modulated by web 14, across the entire width of web 14 for which it is desired to detect defects.

The frame 50 shown in FIG. 3 is constructed from frame blocks 52 each housing four detectors 24. In this manner, groups of detectors 24 may be added or subtracted from the system, depending on the width of web 14. It should be understood, however, that various suitable constructions may be provided. For example, FIG. 1 illustrates a frame 50 in which each frame block 52 houses two detectors.

As shown in FIGS. 1 and 3, each detector 24 is disposed in a transverse position in which its sensor 28 is aligned transverse to the path of travel 20 of web 14. Because of the overlapping arrangement of the detector sensor areas 48 of the parallel detector rows, the entire width of web 14 may be monitored without movement of the detectors. If the system is used to inspect a woven web having weft elements and perpendicular warp elements, this position permits the system to detect weft element defects. In particular, the sensor areas 48 are generally aligned with the weft elements, for example yarn. Thus, as web 14 moves between the detectors 24 and light elements 52, the web modulates the light from the light elements so that the sensors 48 receive a varying light signal. Specifically, each weft element substantially blocks light, whereas gaps or interfaces between adjacent weft elements permit light, or a greater amount of light, to pass.

Each warp element passes through a substantially constant position between the light elements and the detectors. Thus, although defects in the warp elements may have a slight modulating effect, the weft elements primarily modulate the light signal. Because the control mechanism in this embodiment is configured to detect web defects by monitoring the time varying light signal, the system primarily detects weft defects when the detectors are in the transverse position illustrated in FIGS. 1 and 3. It should be understood, however, that the system in the transverse arrangement may also detect warp element defects when such defects are significant enough to affect the time-varying signal detected by the transverse sensors.

To search primarily for warp element defects, detectors 24 may be rotated 90° so that detection areas 48 of sensors 28 are aligned generally with the path of travel 20 (FIG. 1) of web 14, as shown in FIG. 3. In this longitudinal position, however, the warp elements do not sequentially pass in front of the sensors as do the weft elements and, therefore, do not create a similar time-varying light signal. To create such a signal, and to permit the detectors to operatively scan the entire width of the web, frame 50 is moved back and forth a distance at least sufficient to allow the scanning area of each detector to overlap that of its adjacent detector(s) or those of the proximate detectors in the other detector row.

For example, frame 50 may be reciprocally moved so that the detectors 28 follow reciprocal paths, indicated at arrows 54, thereby allowing the detectors of a detector row to scan the width of web 14. The second detector row scans the same area as the first. Since the rows are offset with respect to each other, system reliability is increased. Alternatively, because of the double row arrangement, the distance each detector is moved may be shortened from that illustrated in FIG. 3, thereby permitting a faster cycle and increasing reliability.

Referring to FIG. 1, frame 52 is slidably disposed on rails 56 so that the frame may be moved reciprocally by a shift mechanism including a motor 58 driving a rack and pinion gear mechanism 60. Motor 58 is controlled by a control mechanism 62 which communicates with the motor by a communication line, indicated at 64. Frame 52 may be reciprocally shifted at any suitable rate, for example ten cycles per second, depending, for example, on the construction and speed of web 14. It should be understood that various suitable oscillatory mechanisms, for example a crankshaft arrangement, may be used to reciprocally shift the frame.

Since, in the illustrated embodiment, the system is arranged to primarily monitor either warp defects or weft defects, two such systems may be employed on the same machine if it is desired to simultaneously monitor for both type of defects. The detectors of one system are arranged in the transverse position, while those of the other system are arranged in the longitudinal position.

Referring again to FIG. 1, detectors 24 receive light passing through web 14 as it moves between the detectors and light elements 52. It should be understood, however, that the present invention may comprise any suitable arrangement in which one or more detectors receive light modulated by a moving web. That is, the detectors receive light with which the moving web interferes so that changes in the light received by the detectors, other than the light's natural variations, indicate changes in the moving web. Accordingly, for example, the detectors may receive light that is reflected from, rather than that passes through, the moving web. Furthermore, the system may monitor any suitable light signal parameter, for example amplitude and/or frequency.

Control mechanism 62 controls each motor 38, and receives the output of sensors 28 from lines 46, over bidirectional control lines 66. Initially, where the web is comprised of weft and warp elements, control mechanism 62 controls the motors to move the detectors to either the transverse position and the longitudinal position discussed above. This may be effected by an operator controlled switch (not shown) which activates a processor of control mechanism 62 to activate appropriate relays to activate the motors. Stops (not shown) within frame 50 may be provided to engage the head of stop screw 42 (FIG. 4) of each detector 24 to restrict the detector's movement about its vertical axis 68 (FIG. 4) to slightly greater than a 90° arc, the opposite extremes of the arc being the transverse position and the longitudinal position, respectively. As explained in more detail below, the control mechanism then automatically makes fine adjustments to the detector's rotational position to align the sensor within the transverse or longitudinal position to optimize the signal received by the detector.

Figure 5:
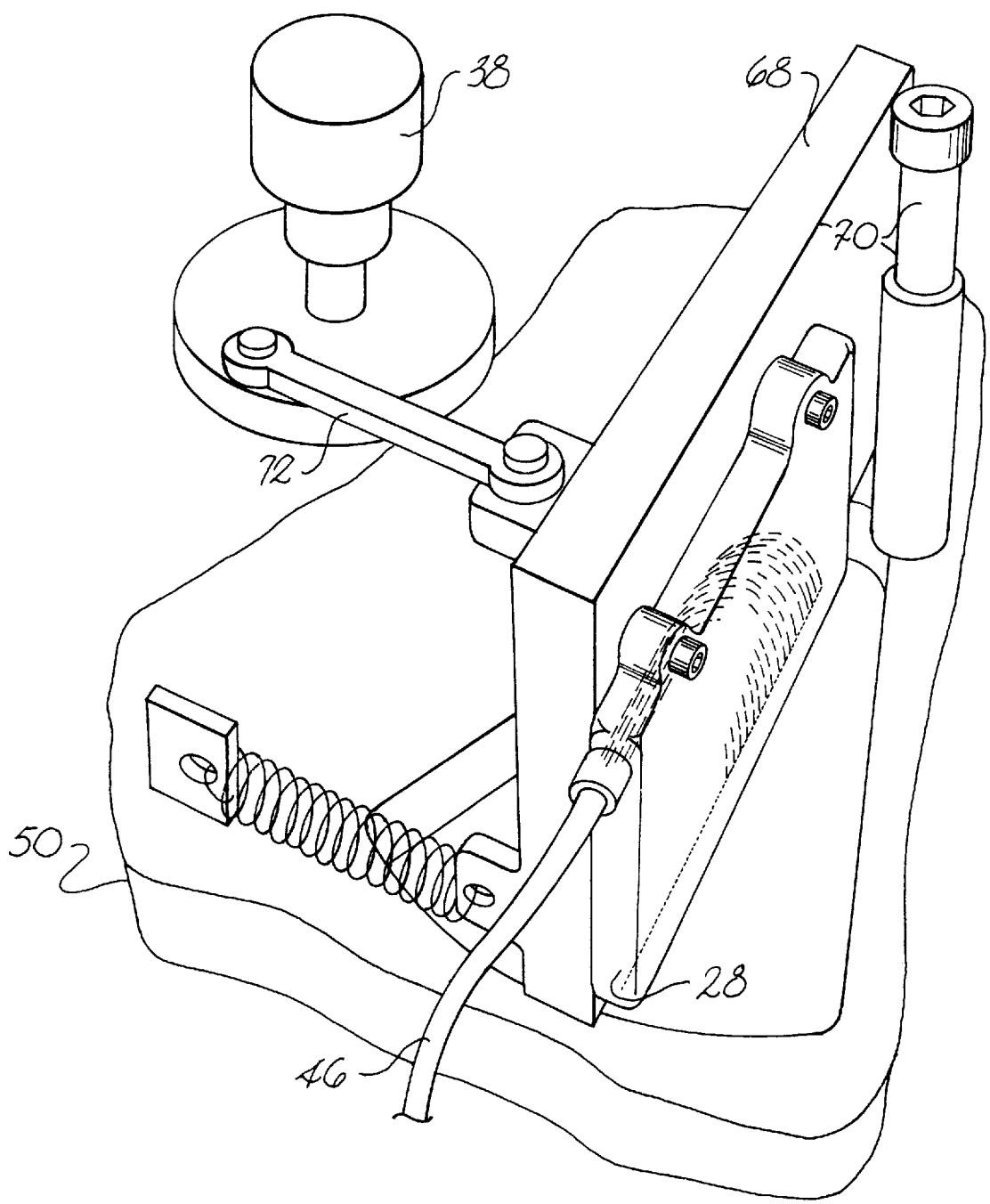
FIG. 5 is a perspective of an embodiment of a detector device and adjusting motor for use in an optical web defect detection system constructed in accordance with the present invention.

One alternate arrangement of the detectors and the adjustment mechanism is illustrated in FIG. 5. Here, frame 50 comprises a flat plate under which web 14 (FIG. 1) passes. A plurality of elongated sensors 28 are secured to respective panels 68 each pivotally mounted to frame 50 by a hinge 70. Motor 38 drives a cam mechanism 72 responsively to a control mechanism 62 (FIG. 1) to align sensor 28 to optimally receive the modulated light signal.

Figure 8:
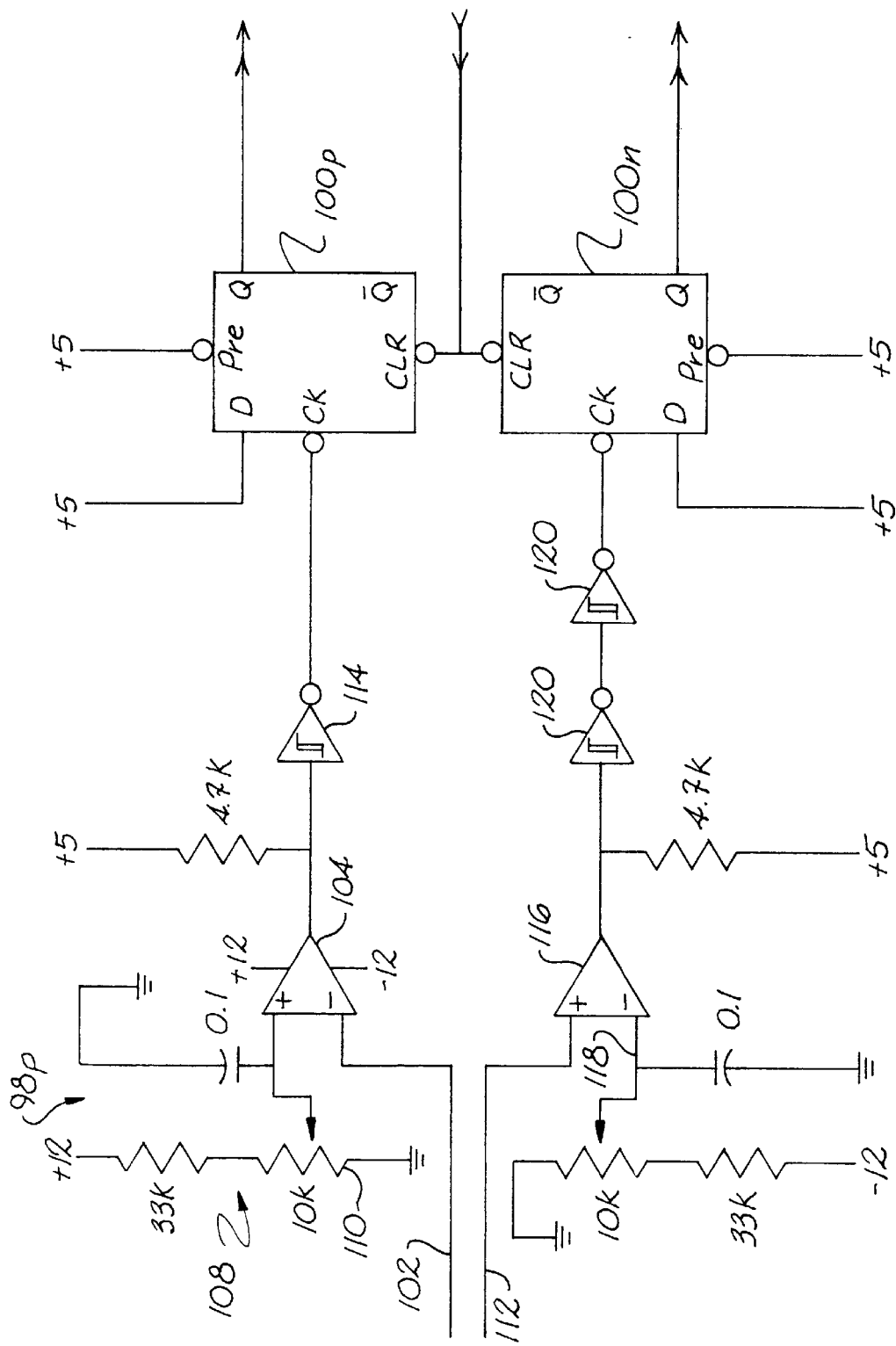
FIG. 8 is a partial schematic illustration of an embodiment of a control mechanism for use in an optical web defect detection system constructed in accordance with the present invention.
Figure 9:
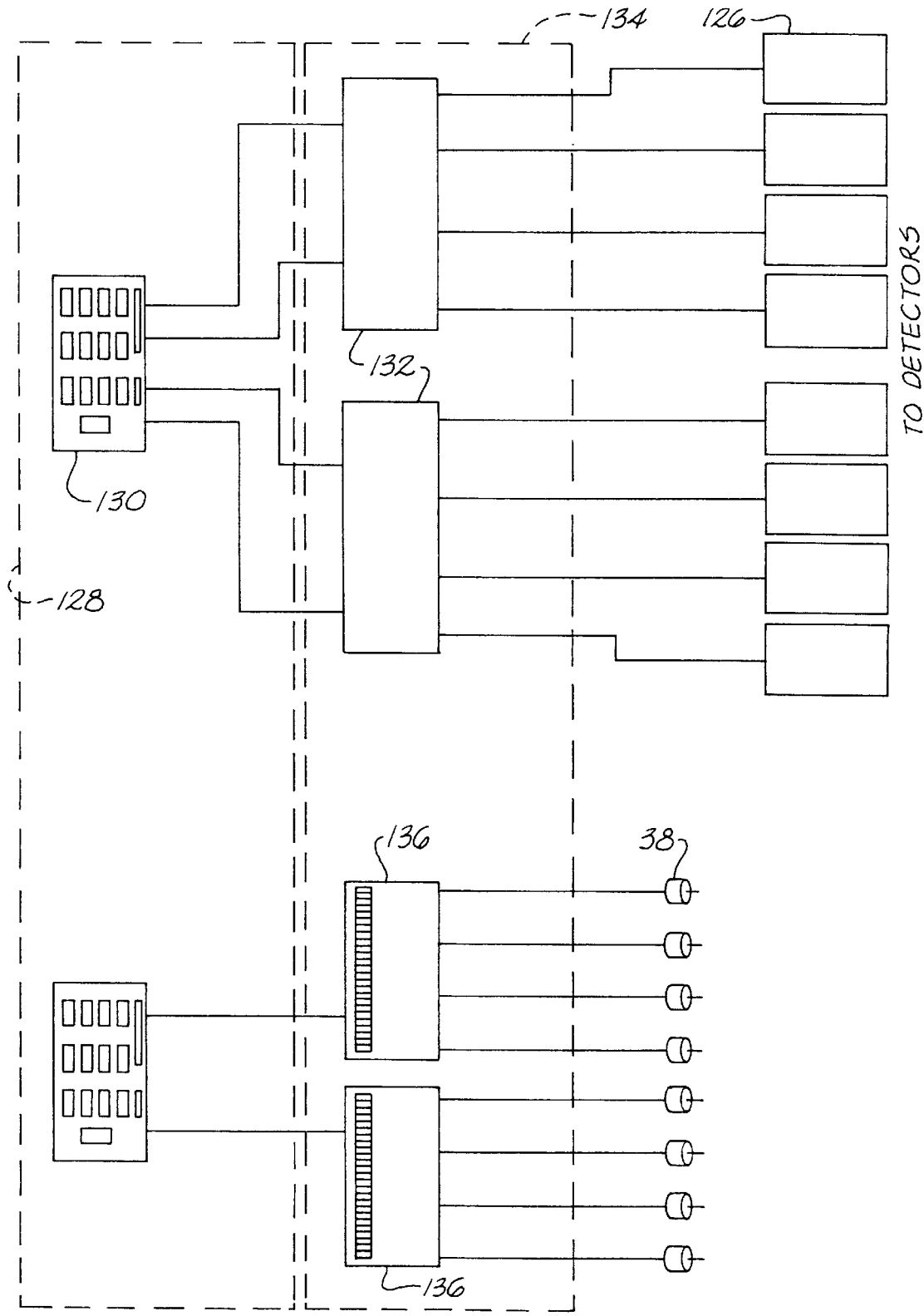
FIG. 9 is a schematic illustration of an embodiment of a control mechanism and adjustment mechanism for use in an optical web defect detection system constructed in accordance with the present invention.
Figure 10:
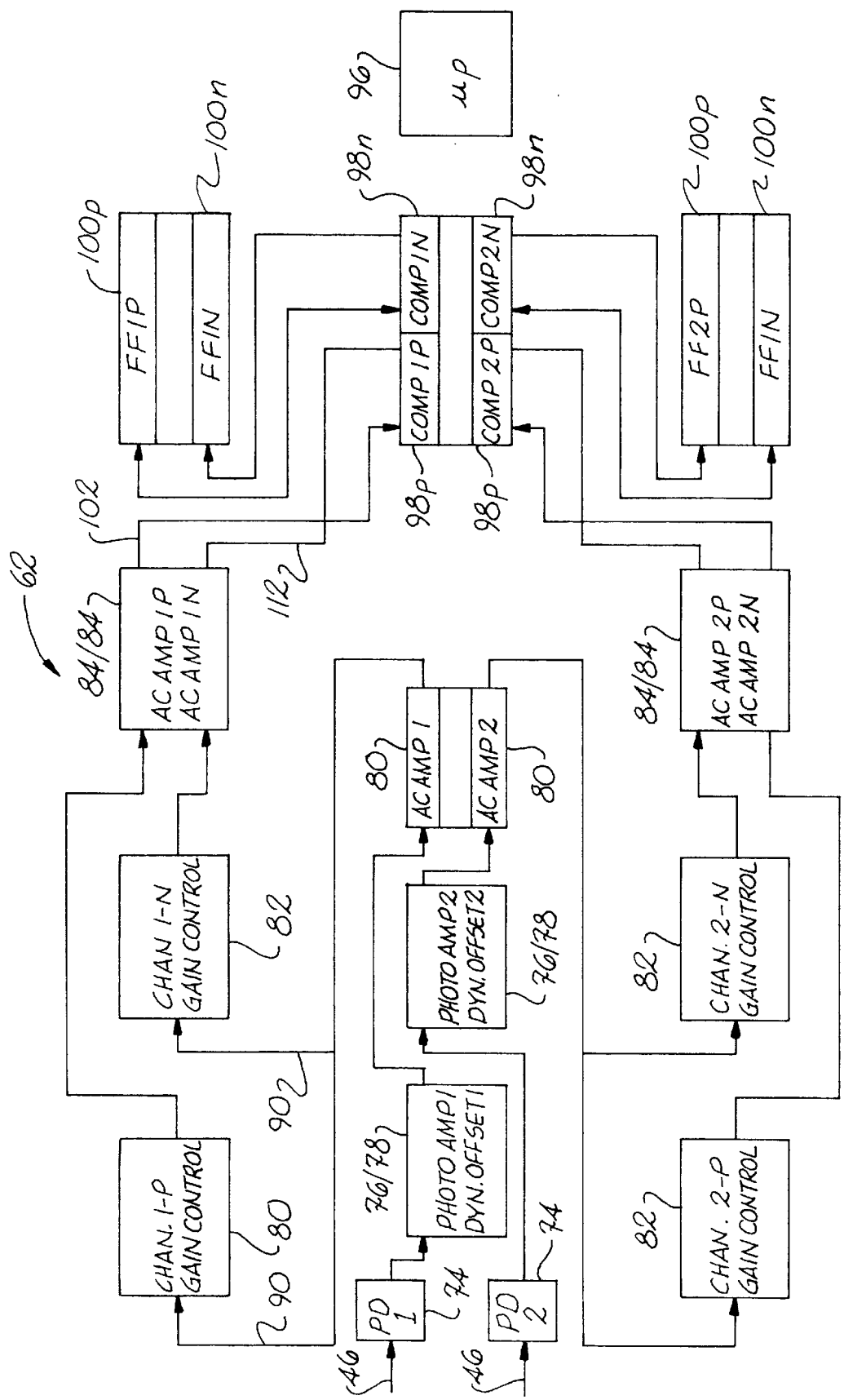
FIG. 10 is a partial block diagram of an embodiment of a control mechanism for use in an optical web defect detection system constructed in accordance with the present invention.

The control mechanism is schematically illustrated in FIGS. 6–10. Initially, FIG. 10 illustrates a control system having a gain stage and a comparator stage for each of two detectors. Each gain stage includes a photoamplifier 76, a dynamic offset 78, a first AC amplifier 80, two adjustable gain control devices 82 and two second AC amplifiers 84. Each comparator stage includes a pair of comparators 98p and 98n and a pair of flip-flops 100p and 100n. It should be understood that this architecture may be repeated for any number of detectors.

Figure 6:
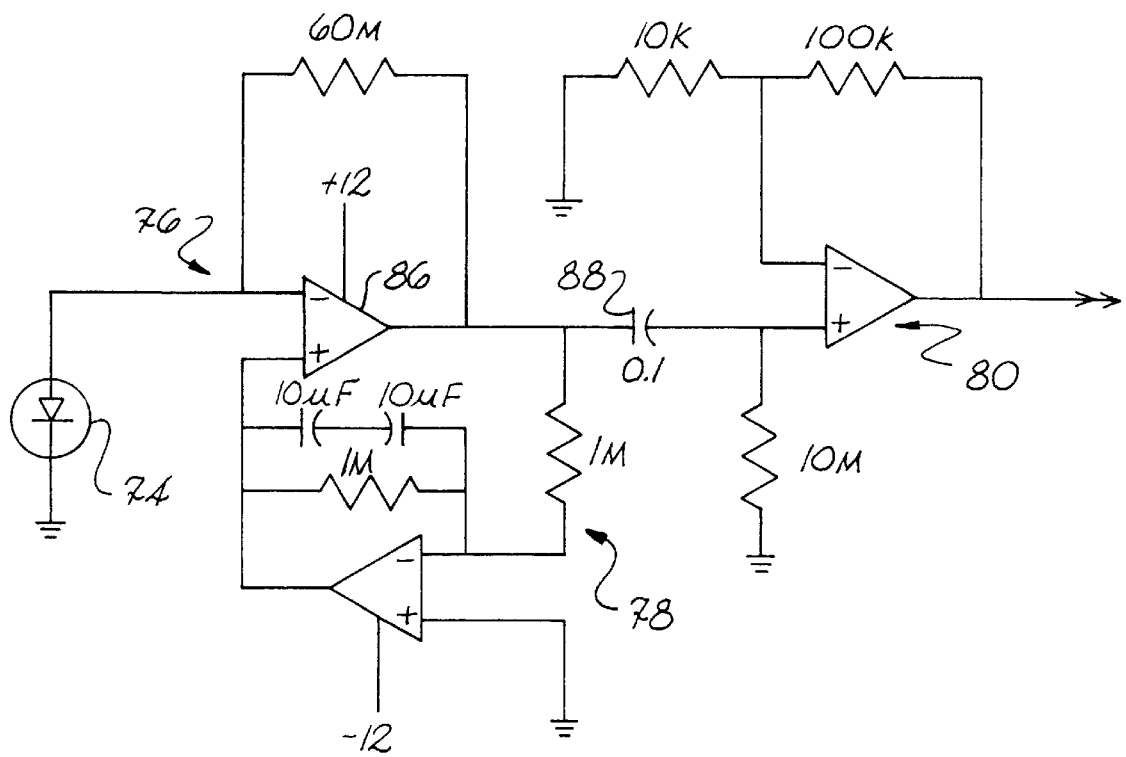
FIG. 6 is a partial schematic illustration of an embodiment of a control mechanism for use in an optical web defect detection system constructed in accordance with the present invention.

Referring also to FIG. 6, each fiber optic bundle 46 feeds to a photodiode 74, which is preferably a sensitive, low noise device, for example a 53374 silicon detector available from Edmund Scientific. Although photodiodes may be preferred in certain circumstances for cost, speed and sensitivity, it should be understood that other devices, such as CCD cameras or line scan cameras, may be used instead of the photodiode. Furthermore, a lens and line scan chip may be mounted on the detector in place of the fiber optic sensor.

The output from diode 74 is directed to op amp 86 which is arranged as a transresistance amplifier. To remove DC signal components and low frequency ambient light variations, for example due to changes in web style or density or to aging of the light elements, dynamic offset circuit 78 feeds back the amplifier output. Dynamic offset circuit 78 operates under an approximately one second time constant, causing the op amp to subtract DC components and low-frequency light changes from the photodiode output. Accordingly, the output of amplifier 86 is approximately equal to the AC component of the photodiode output.

As noted above, the light signal reaching the fiber optic detector is at a minimum when a web element passes directly beneath the sensor and is at a maximum as a gap or interface between adjacent elements passes beneath the sensor. The result is the same whether the detectors are in the transverse position, where the weft elements pass beneath the sensors, or in the longitudinal position, where the detectors are moved reciprocally over the warp elements. Since the dynamic offset circuit removes DC and low frequency AC components from the photodiode output, the output of amplifier 86 is that part of the photodiode output corresponding to the modulated light signal from the web and amplified by the transresistance amplifier gain. Capacitor 88 removes any remaining DC component, and the signal output to AC amplifier 80 is a time-varying signal having negative and positive components corresponding to the passage of web elements and the gaps or interfaces therebetween, respectively, under the sensor.

Figure 7:
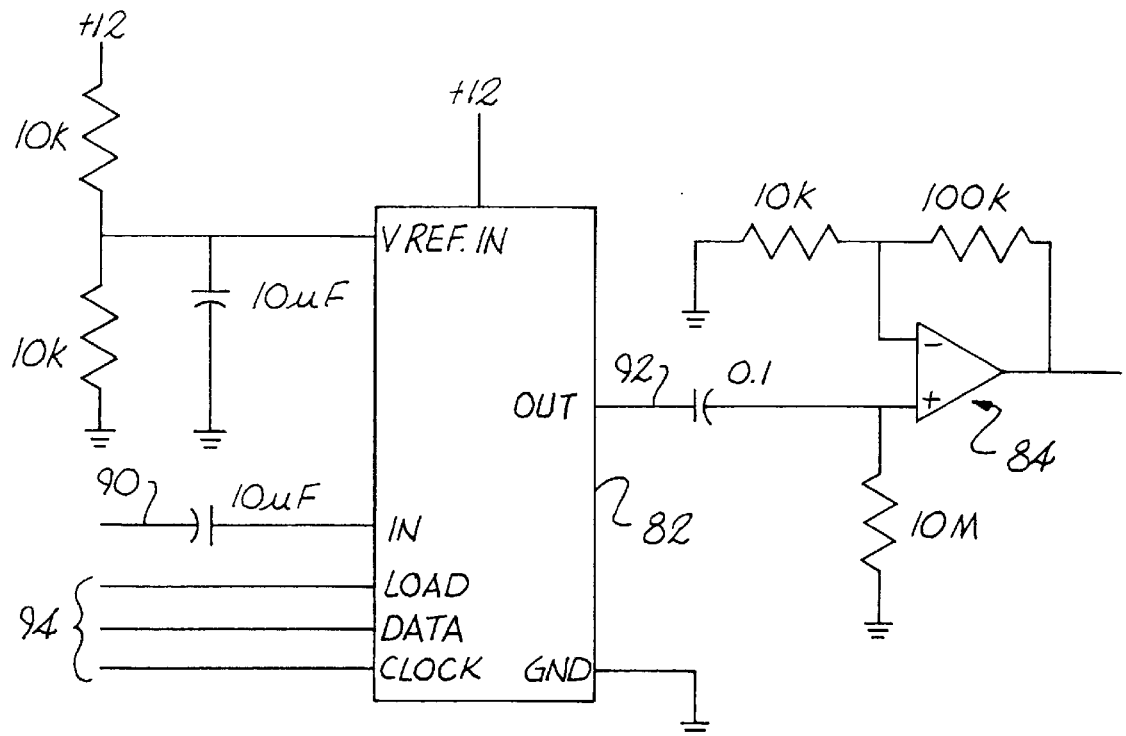
FIG. 7 is a partial schematic illustration of an embodiment of a control mechanism for use in an optical web defect detection system constructed in accordance with the present invention.

AC amplifier 80 amplifies this time-varying signal by a factor of ten, outputting the amplified signal to the input 90 of adjustable gain device 82 as shown in FIG. 7. While FIG. 10 illustrates two adjustable gain control devices and AC amplifiers per detector, the construction and arrangement of each such pair is identical. For purposes of clarity, therefore, FIG. 7 illustrates only one pair.

In the illustrated embodiment, adjustable gain device 82 is an attenuator which receives input 90 and outputs a signal at 92 attenuated by a factor determined by the setting of control lines 94. AC amplifier 84 is identical to amplifier 80, again amplifying its input signal by a factor of ten.

Referring again to FIG. 10, signal 90 is directed to separate channels, each having an attenuator 82 and amplifier 84. This allows separate analysis of the output of amplifier 80 for positive and negative deviations. Accordingly, each block following amplifier 80 is identified as "P" or "N" to identify the block as part of the "positive" or "negative" channel. As is explained in more detail below, this permits the microprocessor 96 to separately control the positive and negative attenuators 82 so that the system accurately detects defects based on positive and negative signal variations.

The outputs of the positive and negative amplifiers 84 are directed to the comparator stage comprising "positive" comparator circuit 98p, "negative" comparator circuit 98n, "positive" flip-flop 100p and "negative" flip-flop 100n. Referring also to FIG. 8, the output 102 from the positive amplifier 84 is input to a comparator 104, which compares the signal to a predetermined voltage at 106. In the illustrated embodiment, voltage 106 is determined by a voltage divider network 108 including a variable resistor 110. It should be understood, however, that this voltage is a reference voltage which might not require adjustment and that the circuit may therefore be arranged so that voltage 106 is invariable.

As shown in FIG. 8, reference voltage 106 is approximately 3 volts. The particular voltage used, however, may depend on the operating range of the components in the upstream circuitry. In particular, the output 102 and 112 of the positive and negative amplifiers 84 (FIG. 10) is generally between approximately −3 and +3 volts.

Comparator 104 goes low whenever the signal on line 102 exceeds the voltage at 106. An inverting Schmitt trigger 114 changes this to a positive signal which is input to flip-flop 100p. When inverter 114 changes state, flip-flop 100p output Q becomes equal to input D, here set to positive five volts. Output Q is directed to microprocessor 96 (FIG. 10), thereby allowing the microprocessor to monitor when the signal at 102 exceeds the reference voltage. That is, the microprocessor monitors, by the gain and comparator stages of the control mechanism, a signal corresponding to the modulated light signal received from the moving web to determine when that signal exceeds a predetermined reference level.

To calibrate the control system so that the reference voltage at 106 may be used to determine when a defect has occurred, the microprocessor automatically adjusts the gain of attenuator 82 (FIG. 7). At start-up, for example, the microprocessor sets control lines 94 so that the attenuator is set to its lowest attenuation level. Accordingly, the gain stage is set to its highest gain level. At this point, the positive peak of the signal on line 102 should exceed the reference voltage at 106 (FIG. 8), thereby causing the Q output of flip-flop 100p to change state. In response, the microprocessor clears the flip-flop and increases the attenuation of attenuator 82 by appropriate signals over the control lines. The microprocessor continues this process, clearing the flip-flop approximately ten times per second and increasing the attenuation of the attenuator at approximately 1 dB steps until flip-flop 100p (FIG. 8) fails to change state.

At the end of this first calibration stage, any increase in the positive peak of the modulated light signal from the web causes flip-flop 100p to change state. From experience, however, it may be determined that an increase of a certain percentage above this level indicates a defect, for example a mispick or a thin place, that justifies notification of an operator. Accordingly, in a second calibration stage, microprocessor 96 (FIG. 10) further steps the attenuation level of the attenuator so that the peak of the signal on line 102 must exceed its normal value by this percentage before flip-flop 100p is triggered. Following this self-calibration, therefore, a change of state of flip-flop 100p notifies the microprocessor that a defect has occurred, permitting microprocessor to initiate notification of an operator, as discussed in more detail below.

Referring again to FIGS. 8 and 10, a similar arrangement of comparator circuit 98n and flip-flop 100n provides notification of defects through analysis of the amplifier 84 output from line 112. Specifically, the amplifier output on line 112 is compared by a comparator 116 to a negative reference voltage at 118 (approximately −3 volts in the illustrated embodiment) so that comparator 116 goes high when ever the amplifier output on line 112 drops below this voltage. A pair of inverting Schmitt triggers 120 is provided to assure a clean transition of the signal as it is directed to flip-flop 100n.

Microprocessor 96 calibrates the negative channel as it calibrates the positive channel, simultaneously resetting the flip-flop 100p and 100n and simultaneously stepping each attenuator until the first of the flip-flops stops triggering. The microprocessor continues stepping the attentuator for the other channel until its flip-flop also ceases to trigger. Ideally, however, both flip-flops should become stable at approximately the same time.

Defects, such as double picks or over-thick web elements, that tend to increase the negative peak may have a greater or lesser effect on the negative signal peak than positive-related defects, such as mispicks, have on the positive signal peak. Thus, the microprocessor may be programmed to set different final attenuation levels for the positive channel attentuator and the negative channel attentuator.

Once the system detects a defect, the microprocessor activates an alarm mechanism, for example a dye spray nozzle 122 over a communication line 124 (FIG. 1), which marks the selvage proximate the defect. The dye mark may be mechanically or visually detected so that this portion of the web may be removed prior to finishing or sale. Other alarm mechanisms may include, for example, audible or visual alarms or machine controls to automatically stop the machine.

FIG. 9 illustrates a block diagram of the hardware components of control mechanism 62. The gain stage and comparator stage for each detector are constructed on respective circuit boards 126. Accordingly, the arrangement illustrated in FIG. 9 accommodates eight detectors. Depending on the components used, however, multiple gain and comparator stages may be mounted on a single board. For example, if the configuration of FIG. 10 is mounted on a single board 126, the arrangement of FIG. 9 accommodates sixteen detectors. Input/output cards 130 plug into a PC 128 to allow boards 126 to communicate with the microprocessor through termination boards 132 of an input/output cabinet 134.

The microprocessor may be housed in any conventional computing device, for example a custom built system including a microprocessor and various memory and input/output devices. Furthermore, however, the system may employ a conventional personal computer 128 having standard input/output ports and operating systems. Regardless of the platform, those of ordinary skill in the art should understand that the computing device may be programmed so that the microprocessor is able to execute the functions described above.

The microprocessor also controls servo motors, for example unipolar stepper motors, 38 through relay modules 136. For example, simultaneously with the first self-calibration of the control mechanism described above, the rotational position of the detectors is automatically calibrated to maximize the signal strength received by the detectors. More specifically, as the system steps through the attenuation levels to determine when the flip-flops stop triggering, it uses this information to simultaneously calibrate the detector position.

In one embodiment, the microprocessor calibrates the rotational position of each detector by monitoring the output of its respective flip-flop 100p (FIG. 8). Assuming that the detector is in either the longitudinal or the transverse position, each detector is initially positioned at an extreme end of its 90° arc, and its positive channel attenuator is set to its lowest attenuation level. That is, the positive channel gain is set to the highest level. With the web running underneath the detectors, each positive channel attenuator is stepped through increasing attenuation levels until the positive channel flip-flop ceases to trigger. This is the first stage of the control mechanism calibration discussed above. At this point, the control mechanism rotates the detector's motor 38 about axis 68 (FIG. 4) by a predetermined increment, for example 0.9°.

If the modulated light's signal strength is higher at this position, the positive flip-flop triggers, and the attenuator is again stepped to higher attenuation levels until the flip-flop again ceases to trigger. If the flip-flop doesn't trigger at the new position, the motor is incremented again, and the process is repeated through a predetermined range of rotation of the motor, for example approximately 18°. At the completion of this arc, the detector is returned to the last position at which the positive flip-flop triggered. This is the position at which the detector received the strongest modulated light signal with respect to the positive peak. Accordingly, the position of the detector has been adjusted to optimize reception of the modulated light, in this case with respect to the positive signal portion.

Accordingly, when the system simultaneously calibrates the control mechanism and the detector position, the process of stepping through attenuation levels until the flip-flop becomes stable is repeated at incremental detector positions. This extends the first calibration stage of the control mechanism. Following this stage, as described above, the microprocessor sets the final attenuation level for the positive channel and negative channel attentuators, and the system searches for web defects.

Control mechanism self-calibration may occur repeatedly during machine operation, for example periodically or intermittently after start-up, and/or at changes of the web. Calibration subsequent to start-up may or may not include detector position self-calibration, depending on the needs of the operator or the requirements of a particular configuration.

In another preferred embodiment, the detector position calibration is independent of the control mechanism calibration. In this embodiment, an analog-to-digital converter samples the AC signal corresponding to the modulated light signal at some point in the gain stage, for example following amplifiers 76, 80 or 84 (FIGS. 6 and 7), and outputs to the microprocessor a digital signal corresponding to the AC component of the modulated light signal. As before, the detector begins at one extreme of its 90° rotational arc, depending on whether the detector is in the transverse or the longitudinal position. If the converter samples the signal upstream from the attenuator, the attenuator setting is unimportant. If the converter samples the signal downstream from the attenuator, however, the attenuator setting is maintained at an arbitrary level. The detector is then incrementally rotated through a predetermined arc, for example 18°, while the microprocessor measures the positive signal peak at each step. At the end of the arc, the detector is returned to the position at which the highest peak was measured.

Each detector position calibration method described above is based on the positive signal peak. It should be understood, however, that either method may base the calibration on the negative peak, for example by monitoring the output of the negative channel flip-flop or by monitoring the negative peak from the analog-to-digital converter. Furthermore, the system may monitor both the positive and negative signal portions and determine the appropriate position for the detector based on the greatest signal magnitude.

While one or more preferred embodiments of the invention have been described above, it should be understood that any and all equivalent realizations of the present invention are included within the scope and spirit thereof. Thus, the embodiments depicted are presented by way of example only and are not intended as limitations upon the present invention, and those of ordinary skill in this art should understand that many modifications may be made. Therefore, it is contemplated that any and all such embodiments are included in the present invention as may fall within the literal or equivalent scope of the appended claims.

What is claimed is:

1. An optical web defect detection system, said system comprising:
   a light source;
   a detector disposed with respect to said light source so that said detector receives light modulated by a moving web proximate said light source, wherein said detector outputs a signal corresponding at least in part to said modulated light;
   an adjustment mechanism in operative communication with said detector to adjust the position of said detector with respect to said web; and
   a control mechanism in operative communication with said detector and said adjustment mechanism, said control mechanism receiving said signal to detect a defect in said web based thereon and adjusting said position of said detector to optimize reception of said modulated light by said detector.

2. The system as in claim 1, wherein said adjustment mechanism includes a motor.

3. The system as in claim 1, wherein said control mechanism is configured, in conjunction with said adjustment mechanism, to incrementally adjust said position of said detector.

4. The system as in claim 1, wherein said detector includes an elongated optical sensor and wherein said control mechanism is configured, in conjunction with said adjustment mechanism, to adjust said position of said detector to align said optical sensor with elements of said web to maximize reception of said modulated light by said optical sensor.

5. The system as in claim 4, wherein said control mechanism rotates said optical sensor about a transverse axis of said optical sensor normal to a longitudinal axis of said optical sensor and to said web to adjust said position of said detector.

6. The system as in claim 4, including a plurality of said detectors disposed proximate to each other to extend across the path of travel of said web.

7. The system as in claim 6, wherein each said detector is positionable to a transverse position in which said elongated optical sensor is aligned transversely to said path of travel of said web so that said optical sensors of said plurality of detectors receive said modulated light from an area of said web extending substantially across said web.

8. The system as in claim 6, wherein each said detector is positionable to a longitudinal position in which said elongated optical sensor is aligned longitudinally to said path of travel of said web.

9. The system as in claim 8, including a shift mechanism in communication with said plurality of detectors and configured to reciprocally move said detectors a predetermined distance transverse to said path of travel of said web when said detectors are in said longitudinal position so that said plurality of detectors receives said modulated light from an area of said web extending substantially across said web.

10. The system as in claim 9, wherein said detectors are mounted on a frame disposed proximate said path of travel of said web and movable transversely with respect to said path of travel of said web, and wherein said shift mechanism is in driving engagement with said frame.

11. The system as in claim 10, wherein said shift mechanism includes a rack and pinion gear assembly in driving engagement with said frame, and a motor operatively driving said gear assembly.

12. The system as in claim 1, wherein said control mechanism includes a processor and an adjustable gain device receiving said signal and wherein said processor adjusts said adjustable gain device so that said signal is amplified to a predetermined level.

13. The system as in claim 12, wherein said adjustable gain device is an attenuator.

14. The system as in claim 12, wherein said control mechanism includes a gain stage and a comparator stage, wherein said gain stage includes said adjustable gain device, wherein said comparator stage compares said amplified signal to at least one reference signal, and wherein said processor detects a defect in said web based on said comparison between said amplified signal and said at least one reference signal.

15. The system as in claim 14, wherein said comparator stage includes a comparator receiving said amplified signal and comparing said amplified signal to a positive said reference signal so that said comparator changes state when said amplified signal exceeds said positive reference signal.

16. The system as in claim 14, wherein said comparator stage includes a comparator receiving said amplified signal and comparing said amplified signal to a negative said reference signal so that said comparator changes state when said amplified signal drops below said negative reference signal.

17. The system as in claim 1, wherein said control mechanism is configured to amplify said signal and to detect a defect in said web based on the amplitude of said signal.

18. The system as in claim 1, including an alarm mechanism in operative communication with said control mechanism and configured to notify an operator responsive to said control mechanism upon detection of a said defect.

19. The system as in claim 18, wherein said alarm mechanism comprises a dye spray mechanism configured to mark said web proximate a said defect detected by said control mechanism.

20. The system as in claim 1, wherein said control mechanism includes a filter configured to remove DC components and low-frequency ambient light components present in said signal.

21. An optical web defect detection system, said system comprising:
   a light source;
   a plurality of detectors disposed proximate to each other to extend across the path of travel of a moving web, each said detector having an elongated optical sensor disposed so that said sensor receives light modulated by said web moving between said detector and said light source, wherein each said detector outputs a signal at least in part corresponding to said modulated light received by its said sensor;
   an adjustment mechanism in operative communication with said detector to adjust the position of said detector with respect to said web; and
   a control mechanism in operative communication with said detector and said adjustment mechanism, said control mechanism being configured to adjust, in conjunction with said adjustment mechanism, said position of each said detector to align its said sensor with elements of said web to maximize reception of said modulated light by said sensor, and including
   a gain stage receiving said signals from said plurality of detectors and having at least one adjustable gain device,
   at least one processor that adjusts said at least one adjustable gain device so that said signals are amplified to a predetermined level, and
   a comparator stage that compares each said amplified signal to at least one reference signal,
   wherein said at least one processor detects a defect in said web based on said comparison by said comparator stage.

22. The system as in claim 21,
   wherein each said detector is positionable to a transverse position in which its said elongated optical sensor is aligned transversely to said path of travel of said web so that said optical sensors of said plurality of detectors receive said modulated light from an area of said web extending substantially across said web,
   wherein each said detector is positionable to a longitudinal position in which its said elongated optical sensor is aligned longitudinally to said path of travel of said web, and
   wherein said system includes a shift mechanism in communication with said plurality of detectors and configured to reciprocally move said detectors a predetermined distance transverse to said path of travel of said web when said detectors are in said longitudinal position so that said plurality of detectors receives said modulated light from an area of said web extending substantially across said web.

23. The system as in claim 21, wherein
   said gain stage includes a plurality of said adjustable gain devices, each said adjustable gain device receiving a said signal from a respective one of said detectors,
   said comparator stage includes a plurality of first comparators, each said first comparator receiving said amplified signal from a respective said adjustable gain device and comparing said amplified signal to a positive said reference signal so that said first comparator changes state when said amplified signal exceeds said positive reference signal, and
   said comparator stage includes a plurality of second comparators, each said second comparator receiving said amplified signal from a respective said adjustable gain device and comparing said amplified signal to a negative said reference signal so that said second comparator changes state when said amplified signal drops below said negative reference signal.

24. The system as in claim 21, including an alarm mechanism in operative communication with said control mechanism and configured to notify an operator responsive to said control mechanism upon detection of a said defect.

25. The system as in claim 21, wherein said control mechanism includes a filter configured to remove DC components and low-frequency ambient light components present in said signal.

26. An optical web defect detection system, said system comprising:
   a light source;
   a plurality of detectors disposed proximate to each other to extend across the path of travel of a moving web, each said detector having an elongated optical sensor disposed so that said sensor receives light modulated by said web moving between said detector and said light source, wherein each said detector outputs a signal corresponding at least in part to said modulated light received by its said sensor;
   an adjustment mechanism in operative communication with said detector to adjust the position of said detector with respect to said web;
   a control mechanism in operative communication with said detector and said adjustment mechanism, said control mechanism being configured to selectively adjust, in conjunction with said adjustment mechanism, said position of each said detector
      to a transverse position in which its said elongated optical sensor is aligned transversely to said path of travel of said web so that said optical sensors of said plurality of detectors receive said modulated light from an area of said web extending substantially across said web, and
      to a longitudinal position in which its said elongated optical sensor is aligned longitudinally to said path of travel of said web,
   wherein said control mechanism is also configured to adjust, in conjunction with said adjustment mechanism, said position of each said detector in either of said transverse position and said longitudinal position to align its said sensor with elements of said web to maximize reception of said modulated light by said sensor,
   wherein said control mechanism includes
      a gain stage having a plurality of adjustable gain devices, each said adjustable gain device receiving said signal from a respective one of said detectors,
      at least one processor that adjusts each said adjustable gain device so that said signal received by said adjustable gain device is amplified to a predetermined level, and
      a comparator stage receiving said amplified signal from each said adjustable gain device, said comparator stage including
         a plurality of first comparators, each said first comparator receiving said amplified signal from a respective said adjustable gain device and comparing said amplified signal to a positive said reference signal so that said first comparator changes state when said amplified signal exceeds said positive reference signal, and
         a plurality of second comparators, each said second comparator receiving said amplified signal from a respective said adjustable gain device and comparing said amplified signal to a negative said reference signal so that said second comparator changes state when said amplified signal drops below said negative reference signal, and wherein said at least one processor detects a defect in said web based on whether one or more of said first comparators and said second comparators change state;

a shift mechanism in communication with said plurality of detectors and said control mechanism and configured to reciprocally move said detectors a predetermined distance transverse to said path of travel of said web when said detectors are in said longitudinal position so that said plurality of detectors receives said modulated light from an area of said web extending substantially across said web; and an alarm mechanism in operative communication with said control mechanism and configured to notify an operator responsive to said control mechanism upon detection of a said defect.

27. A system for handling and inspecting a web of indeterminate length, said system comprising:

a frame configured to secure said web and move said web along a path of travel;

a light source disposed on said frame;

a detector disposed on said frame with respect to said light source so that said detector receives light modulated by a moving web proximate said light source, wherein said detector outputs a signal corresponding at least in part to said modulated light;

an adjustment mechanism in operative communication with said detector to adjust the position of said detector with respect to said web; and a control mechanism in operative communication with said detector and said adjustment mechanism, said control mechanism receiving said signal to detect a defect in said web based thereon and adjusting said position of said detector to optimize reception of said modulated light by said detector.

28. The system as in claim 27, wherein said light source is disposed on one side of said path of travel of said web and said detector is disposed on the other side of said path of travel of said web.

29. The system as in claim 28, including a plurality of said detectors disposed proximate to each other to extend across said path of travel of a moving web, each said detector having an elongated optical sensor disposed so that said sensor receives said modulated light, wherein said control mechanism is configured to adjust, in conjunction with said adjustment mechanism, said position of each said detector to align its said sensor with elements of said web to maximize reception of said modulated light by said sensor, and wherein said control mechanism includes a gain stage receiving said signals from said plurality of detectors and having at least one adjustable gain device, at least one processor that adjusts said at least one adjustable gain device so that said signals are amplified to a predetermined level, and a comparator stage that compares each said amplified signal to at least one reference signal, wherein said at least one processor detects a defect in said web based on said comparison by said comparator stage.

30. The system as in claim 29, wherein each said detector is positionable to a transverse position in which its said elongated optical sensor is aligned transversely to said path of travel of said web so that said optical sensors of said plurality of detectors receive said modulated light from an area of said web extending substantially across said web, wherein each said detector is positionable to a longitudinal position in which its said elongated optical sensor is aligned longitudinally to said path of travel of said web, and wherein said system includes a shift mechanism in communication with said plurality of detectors and configured to reciprocally move said detectors a predetermined distance transverse to said path of travel of said web when said detectors are in said longitudinal position so that said plurality of detectors receives said modulated light from an area of said web extending substantially across said web.

31. The system as in claim 29, wherein said gain stage includes a plurality of said adjustable gain devices, each said adjustable gain device receiving said signal from a respective one of said detectors, said comparator stage includes a plurality of first comparators, each said first comparator receiving said amplified signal from a respective said adjustable gain device and comparing said amplified signal to a positive said reference signal so that said first comparator changes state when said amplified signal exceeds said positive reference signal, and said comparator stage includes a plurality of second comparators, each said second comparator receiving said amplified signal from a respective said adjustable gain device and comparing said amplified signal to a negative said reference signal so that said second comparator changes state when said amplified signal drops below said negative reference signal.

32. The system as in claim 29, including an alarm mechanism in operative communication with said control mechanism and configured to notify an operator responsive to said control mechanism upon detection of a said defect.

33. A method for optically detecting defects in a moving web, said method comprising:

moving a web proximate a light source;

receiving light by a detector disposed proximate said light source so that said detector receives light modulated by said moving web;

outputting a signal from said detector to a control mechanism so that said signal corresponds at least in part to said modulated light;

detecting defects in said web based on said signal; and controlling, by said control mechanism, the position of said detector based on said signal to optimize reception of said modulated light by said detector.

34. The method as in claim 33, wherein the position of said detector is controlled in said controlling step to maximize reception of said modulated light.

35. The method as in claim 33, including comparing said signal to at least one reference signal and detecting said defects based on said comparison.

36. The method as in claim 33, including amplifying said signal prior to said detecting step.

37. The method as in claim 33, including, prior to said detecting step, removing DC components and low-frequency ambient light components present in said signal.

* * * * *